(12) United States Patent
Borody et al.

(10) Patent No.: US 6,649,360 B2
(45) Date of Patent: Nov. 18, 2003

(54) TEST STRIP FOR DETECTING GASTRIC PROBLEMS BASED ON THE PRESENCE OF UREASE

(75) Inventors: Thomas Julius Borody, 49 Hilly Street, Mortlake, NSW 2137 (AU); Nicolas Peter Shortis, Dural (AU)

(73) Assignee: Thomas Julius Borody, Mortlake (AU)

( * ) Notice: Subject to any disclaimer, the term of this patent is extended or adjusted under 35 U.S.C. 154(b) by 0 days.

(21) Appl. No.: 09/970,415

(22) Filed: Oct. 2, 2001

(65) Prior Publication Data

US 2003/0068656 A1 Apr. 10, 2003

(51) Int. Cl.[7] ............................................. G01N 33/554
(52) U.S. Cl. ..................... 435/7.32; 435/4; 435/12; 435/34; 436/518; 422/55; 422/56; 422/57; 422/58; 422/61
(58) Field of Search ............................ 435/4, 5, 7.32, 435/12, 34; 436/518; 422/55, 56, 57, 58, 61

(56) References Cited

U.S. PATENT DOCUMENTS

| 4,748,113 A | 5/1988 | Marshall |
| 5,314,804 A | 5/1994 | Boguslaski et al. |
| 5,420,016 A | 5/1995 | Boguslaski et al. |
| 5,439,801 A | 8/1995 | Jackson |
| 5,593,851 A | 1/1997 | Jackson |

FOREIGN PATENT DOCUMENTS

| EP | 0 112 077 A1 | 6/1984 |
| EP | 0 369 292 A1 | 5/1990 |
| SU | 1507 797 A | 9/1989 |
| WO | WO 94/13830 | 6/1994 |

OTHER PUBLICATIONS

Stephen C. Edberg et al., *Rapid Biochemical Characterization of Haemophilus Species by Using the Micro–ID*, Journal of Clinical Microbiology, vol. 11, No. 1, Jan. 1980, pp. 22–26.

Joyce Wolfe et al., *A Comparison of Three Methods for the Detection of Urease Activity in Mycobacteria*, Canadian Journal of Medical Technology, vol. 45, 1983, pp. 103–109.

Primary Examiner—Jeffrey Stucker
(74) Attorney, Agent, or Firm—Knobbe Martens Olson & Bear LLP

(57) ABSTRACT

A testing apparatus for detecting urease in a gastric material taken from a human or lower animal subject is disclosed, the apparatus comprising a dry indicating composition responsive to urease, a backing sheet supporting the dry indicating composition, and a cover sheet sealingly adhered about its periphery to the backing sheet to enclose the dry indicating composition. At least one of the backing sheet or cover sheet has a transparent portion in alignment with the dry indicating composition, and wherein the cover sheet may be peeled from the backing sheet and resealed.

17 Claims, 2 Drawing Sheets

TEST STRIP FOR DETECTING GASTRIC PROBLEMS BASED ON THE PRESENCE OF UREASE

TECHNICAL FIELD

The present invention relates to a testing apparatus or diagnostic device suitable for use in diagnosing disorders in humans or lower mammal subjects. In particular the present invention is directed towards a testing apparatus suitable for diagnosis of gastrointestinal disorders by detection of the urease enzyme.

BACKGROUND OF THE INVENTION

*Helicobacter pylori* (*H. pylori*) has been implicated in causing chronic histological gastritis. Its causal role in peptic ulceration is also apparent, but less clear in relation to non-ulcer dyspepsia. The role of *H. pylori* can be more effectively controlled if a quick, inexpensive testing apparatus for detecting it is used. Upon detection or exclusion of *H. pylori*, therapeutic options can be effected to eradicate the infection or treat the symptoms if the infection is excluded.

As with the management of any disorder, the rapid, precise, and accurate diagnosis of gastrointestinal disorders is of paramount importance. However, the diagnostic methods typically employed in the art, such as histopathology, are often slow, cumbersome, costly and may yield equivocal or inaccurate results.

*Helicobacter pylori* can be detected by blood test for antibodies. However, the blood test can remain positive for many months after the bacteria have been eradicated so that checking a patient's success in eradicating the bacteria is not possible. Furthermore, the presence of antibodies presents a falsely positive result in approximately 10 to 15% of patients due to cross reaction with other antibodies.

Other methods for detecting *H. pylori* include the $^{13}C$ and $^{14}C$ breath tests. These test require the availability of the expensive isotopes $^{13}C$ and $^{14}C$ together with the expertise to carry out the test and the ability to detect the presence of $^{13}C$ and $^{14}C$ using very expensive equipment. This includes gas chromatography or a scintillation counter—both are expensive pieces of equipment. Hence, the direct detection of active *Helicobacter pylori* infection to date has been difficult to achieve unless one can obtain tissue from the stomach.

It is known that gastrointestinal disorders of the upper gastrointestinal tract may be detected and diagnosed by methods and compositions for the detection of urease enzyme in the gastric mucosa or gastric fluid of humans or lower animals. U.S. Pat. No. 4,748,113 (Marshall) describes a test kit for urease enzyme detection. However, this test kit is bulky and requires storage at 2–8° C.

A further test method and kit known as PYLORITEK™ described and claimed in U.S. Pat. Nos. 5,314,804 and 5,420,016 utilises a number of components, such as a test pad incorporating a diffusion element, a reaction chamber and hydration solution. This test kit is also bulky, requires storage at 2–7° C. and not simple to use.

The bulkiness and necessity to refrigerate the above mentioned kits adds expense to the storage and shipping of such kits.

It has been found that the aforesaid limitations of the known kits have imposed limitations on the extent of use of such kits, particularly in environments where storage and shipping is a problem, and an object of the invention is to alleviate that situation.

SUMMARY OF THE INVENTION

The present invention overcomes the disadvantage associated with the necessary refrigeration of the prior art testing kits, by providing a testing apparatus having a dry indicating composition responsive to urease. The present invention resides in the appreciation that a dry indicating composition responsive to urease may be used, and that the moisture content required for the test to take place may be provided by the gastric material sample being tested.

In a first aspect the present invention consists in a testing apparatus for detecting urease in a gastric material taken from a mammal, said apparatus comprising a dry indicating composition responsive to said urease, a backing sheet supporting said dry indicating composition, a cover sheet sealingly adhered about is periphery to said backing sheet to enclose said dry indicating composition, wherein at least one of said backing sheet or said cover sheet has a transparent portion in alignment with said dry indicating composition, and wherein said cover sheet may be peeled from said backing sheet and resealed therewith wherein said testing apparatus can be stored a room temperature.

Preferably said dry indicating composition is absorbed or impregnated into or applied to said backing sheet, or alternatively absorbed or impregnated into or applied to wafer adhered to said backing sheet.

Preferably said wafer or backing sheet to which said dry indicating composition is absorbed or impregnated is of suitable thickness to provide sufficient buffering capacity to neutralize acid present in said gastric material.

Preferably said wafer or backing sheet to which said dry indicating composition is absorbed or impregnated comprises a paper having a weight of at least 70 gsm, more preferably about 90 gsm.

Preferably the dry indicating composition prior to drying comprises a liquid composition of:

(a) urea;
(b) an indicator having a $pK_a$ of from about 6.5 to about 8.5 at an effective concentration; and
said liquid composition has a pH from about 5.0 to about 6.5, being at least about one pH unit lower than the $pK_a$ of said indicator.

Preferably said indicator is present at a concentration of 2 to about 100 milligrams per liter.

Preferably said indicator is one of p-nitrophenol, bromothymol blue, phenol-red, neutral red, quinoline blue, cresol purple and thymol blue.

In a second aspect the present invention consists in a method for detection of a gastrointestinal disorder in a mammal by detection of urease in gastric material of the mammal, comprising the steps of:

(a) obtaining a sample of gastric material from said mammal;
(b) providing a day indicating composition of a testing apparatus for detecting urease in a gastric material taken from a mammal, said apparatus comprising a dry indicating composition responsive to said urease, a backing sheet supporting said dry indicating composition, a cover sheet sealingly adherent about its periphery to said backing sheet to enclose said dry indicating composition, wherein at least one of said backing sheet or said cover sheet has a transparent portion in alignment with said dry indicating composition, and wherein said cover sheet may be peeled from said backing sheet and resealed therewith wherein said testing apparatus can be stored at room temperature; and (c) observing the color of said composition; wherein a change of color of said composition indicates the presence of urease and the existence of a gastrointestinal disorder in the mammal.

In a further aspect the present invention consists in a method for detection of a gastrointestinal disorder in a mammal by detection of urease in gastric material of the mammal, comprising the steps of:
(a) obtaining a sample of gastric material from said subject;
(b) providing a dry indicating composition sealed under a transparent cover, in which prior to drying, said composition comprises:
  (i) urea; and
  (ii) as indicator having a $pH_a$ of from about 5.0 to about 8.5 at an effective concentration;
said composition prior to drying having a pH from about 5.0 to about 6.5, the pH of said composition is at least about one pH unit lower than the $pK_a$ of said indicator;
(c) storing said dry indicating composition at room temperature;
(d) unsealing the transparent cover;
(e) contacting said sample with said dry indicating composition;
(f) re-sealing the transparent cover; and
(g) observing the color of said composition; wherein a change of color of said composition indicates the presence of urease and the existence of a gastrointestinal disorder in the mammal.

Preferably in step (e) said sample of gastric material is applied to one side of a wafer or backing sheet to which said dry indicating composition is absorbed or impregnated, following which said sample permeates said wafer or backing sheet, and in step (g) said color is observed by viewing the opposite side of said wafer or backing sheet to that on which said sample was applied.

MODE OF CARRYING OUT INVENTION

Figure 1:
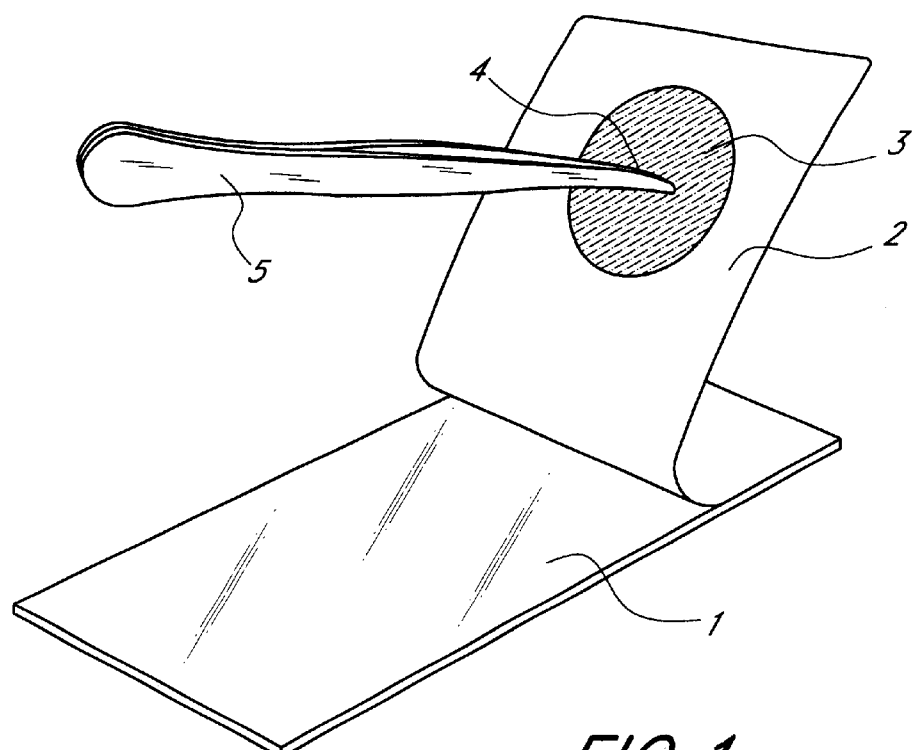
FIG. 1 is a perspective view of a first embodiment of the testing apparatus of the present invention in an open configuration.
Figure 2:
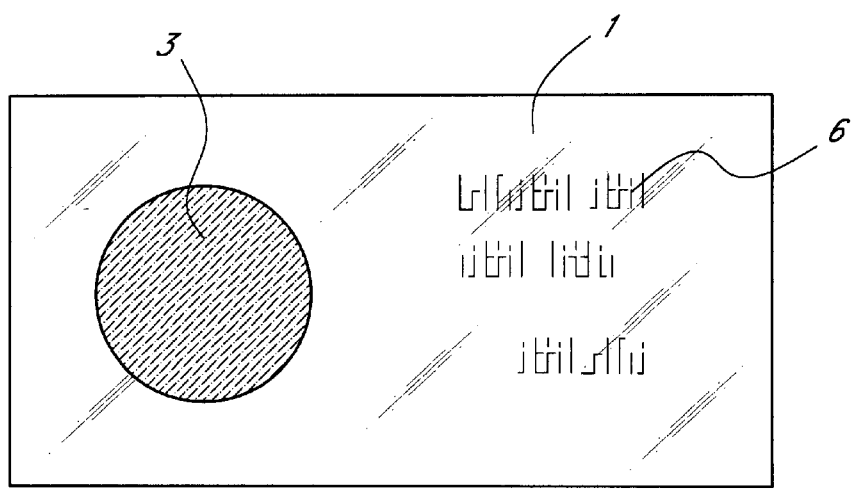
FIG. 2 is a plan view of the testing apparatus shown in FIG. 1 in a closed configuration.

In a first embodiment of the present invention FIG. 1 shows a testing apparatus in an open configuration. The testing apparatus comprises a transparent cover sheet 1 and a backing sheet 2 supporting a wafer 3 carrying a dry indicating composition. The cover sheet 1 and backing sheet 2 are joined at one end and movable with respect to each other, such that wafer 3 may be sandwiched therebetween.

Preferably cover sheet 1 and backing sheet 2 are flexible water impermeable plastic strips. Suitable preferred sizes for such plastic strips are in the range of areas between about 40 square millimeters and 400 square millimeters.

Wafer 3 is adhered to backing sheet 2 and is preferably made of paper or some other suitable material capable of carrying the dry indicating composition by absorption of or impregnation by an initially liquid composition which is then allowed or caused to dry out during manufacture prior to storage and use.

One or both of cover sheet 1 and backing sheet 2 have adhesive on their surfaces which meet when closed together, preferably of the type which remains functionally tacky and allows for repeated openings and closings.

One of both of carrier sheet 1 and backing sheet 2 may carry printed matter 6, such as instructions or other labelling.

Prior to use the testing apparatus is supplied in a closed configuration, such that the dry indicating composition remains sealed and therefore uncontaminated during storage and shipping.

Figure 3:
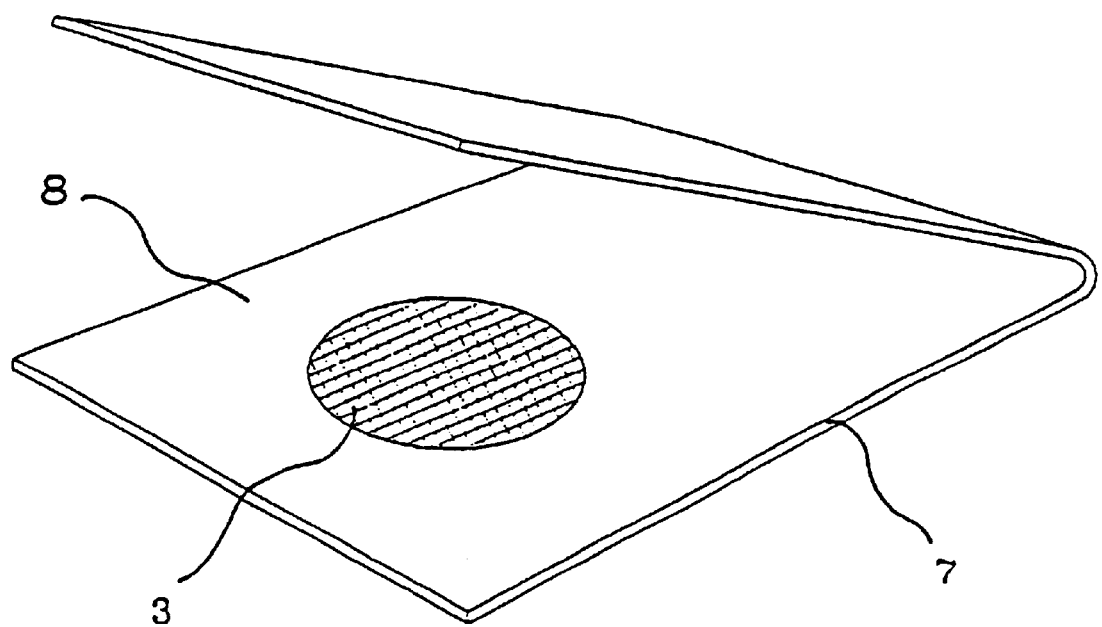
FIG. 3 is a perspective view of a second embodiment of the testing apparatus of the present invention in an open configuration.
Figure 4:
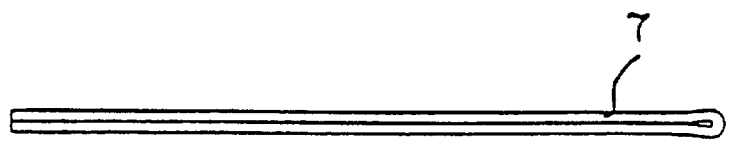
FIG. 4 is an elevational view of the second embodiment of the testing apparatus in a closed configuration.

In a second embodiment as shown in FIGS. 3 and 4, a single sheet 7 may replace the cover and backing sheets of the first embodiment. In such an embodiment single sheet 7 supports wafer 3 and is folded in a manner to provide the function of the cover and backing sheets of the first embodiment and is also similarly provided with an adhesive on surface 8 which remains functionally tacky and allows for repeated openings ad closings of folded sheet 7.

Whilst both first and second embodiments are described with reference to sheets made of plastic strip. It should be understood that other materials may be used in combination with plastic strip. For instance, backing sheet 2 may be paper or some other fibrous material capable of supporting wafer 3. Where paper or fibrous material is used for backing sheet 2, the wafer may be eliminated, and the dry indicating composition may be directly carried on backing sheet 2 by absorption or impregnation. The dry indicating composition whether carried by a wafer of directly by the backing sheet may preferably be between about 5.0 to about 15.0 millimeters in diameter.

In a preferred embodiment the wafer 3, or alternatively the backing sheet 2, carrying the dry indicating composition consists of paper of a suitable thickness to provide a buffering capacity to neutralize acid present in the sample of gastric material as it permeates the wafer 3 or backing sheet 2. Once the sample is contacted with one side of the paper, acid in the sample will cause a color change or 'blush' on that side of the paper. As fluid in the sample permeates the paper acid in the sample is buffered or neutralized. In this regard, the paper will generally contain starch and/or other buffering components that will act to neutralize the acid. It is also within the scope of the present invention to add a buffering agent to the paper. As a result, when the fluid reaches the other side of the paper, the acid is unable to cause a similar color change or 'blush' avoiding the possibility of obtaining a false positive test result.

Preferably the paper or fibrous material of the wafer 3 or backing sheet 2 carrying the dry indicating composition has a weight of at least 70 gsm, more preferably approximately 90 gsm.

The testing apparatus of the present invention is suitable for testing for the presence of urease, in order to diagnose gastrointestinal disorders of human or lower mammal subjects. As used herein, "gastrointestinal disorder" encompasses any disease or other disorder of the gastrointestinal tract of a human or lower mammal. Such gastrointestinal disorders include, for example: disorders not manifested by presence of ulcerations in the gastric mucosa (herein "no-ulcerative gastrointestinal disorder"), including chronic or atrophic gastritis, gastroenteritis, non-ulcer dyspepsia, oesophageal reflux disease and gastric motility disorder, and "peptic ulcer disease" ie, gastric and duodenal ulcers. In particular, "gastrointestinal disorder" refers to such disorders of the upper gastrointestinal tract caused or mediated by bacteria, including Helicobacter-like organisms, eg, *Helicobacter pylori*. Such Helicobacter-like organisms include those described in J. R. Warren and B. J. Marshall, "Unidentified Curved Bacilli on Gastric Epithelium of Campylobacter-like Bacteria that are Distinct from *Campylobacter jejuni*", The Lancet 111–112 (1985).

Testing is achieved by placing a sample of gastric mucosa 4 (or gastric fluid), by means for example using tweezers (or forceps) 5, against the dry indicating composition, closing the sheets together and observing a color change in the dry indicting composition. The transparent nature of cover sheet 1 of the first embodiment or sheet 7 of the second embodiment allows for observation of color change of the indicating composition, whilst keeping the test apparatus closed. Preferably the color change of the indicating composition is viewed from the opposite side of the wafer 3 or backing sheet 2 carrying the indicating solution to the side on which the sample of gastric material was applied.

The test apparatus may be used to test for the presence of urease where the dry indicating composition comprises of urea and an indicator. Urea is of the formula $H_2NCONH_2$, and is a naturally occurring product of protein metabolism. Urea for use in the dry indicating composition, is available from a variety of commercial sources. It is known that gastric materials from humans or other animals having gastrointestinal disorders contain relatively large quantities of urease (urea amidohydrolase), which hydrolyses urea to ammonium carbonate, or ammonia and carbon dioxide. The components of the dry indicating composition serve, in part, to detect the presence of urease through its hydrolysis of urea.

In a preferred embodiment, the initially wet indicating composition prior to "drying" comprises of urea from about 10 to about 40 grams per liter, more preferably from about 20 to about 40 grams per liter, and an indicator having a $pK_a$ of from about 6.5 to about 8.5, at an "effective concentration". The composition should have a pH from about 5.0 to about 6.5, and the pH of the composition is at least about one pH unit lower than the $pK_a$ of the indicator. As used herein, "an effective concentration" of indicator is a concentration of indicator which effects a readily discernible color of the composition when used according to the processes of this invention.

Typically, the indicator is present at a level of from about 2 to about 100 milligrams per liter.

The indicators useful in this invention are weak acids, with sharply different colors in their dissociated (ionised) and undissociated (neutral) states. The indicators useful herein have $pK_a$ values of from about 6.5 to about 8.5, but more preferably from about 7.0 to about 8.0. The color exhibited by the indicator in the present composition will depend on the pH of the composition, the particular indicator used, and the dissociation constant ($K_a$) for that indicator (ie $pK_a = \log_{10} K_a$). As the color exhibited by the indicator changes over a range of pH values ($pH = \log_{10}[H^+]$), the indicators useful in the present composition change color over a pH range of from about 5.5 to about 9.0, preferably from about 6.5 to about 8.5. The pH of the present composition are, accordingly, adjusted to a pH at least about one pH unit lower than the $pK_a$ of the indicator used (ie, having a hydrogen ion concentration [$H^+$] ten times less than (10% of) the hydrogen ion concentration in a solution having a pH equal to the $pK_a$ of the indicator). Preferably, the pH is adjusted to a pH about two pH units below the $pK_a$ of the indicator. Adjustment of the pH of the present compositions can be effected by addition of a base (eg, sodium hydroxide) or an acid (eg, hydrochloride or citric acid). Thus, preferably, the pH of the composition of this invention is adjusted to a pH of from about 5.0 to about 6.5, more preferably from about 5.0 to about 6.0.

Indicators among those useful herein include p-nitrophenol, bromothymol blue, phenol red, neutral red, quinoline blue, cresol purple, and thymol blue. Bromothymol blue, phenol red, neutral red and cresol red are preferred indicators for use in the compositions of this invention. Indicators among those useful herein are described in *The Merck Index* (9th ed. 1976), incorporated by reference herein.

When manufacturing the embodiments of the earlier described test apparatus, the method of "drying" the indicating composition used can be of the order of 30° C. to 80° C. Warm enough so that the paper or other material used in manufacturing the wafer 3 and/or backing sheet 2 is able to dry within a short period of time, yet cool enough so that it does not combust.

The indicating composition may contain additional optional components which affect the performance of physical characteristics of the composition. Such additional components must not, however, interfere with the indicator, ie should not obscure the colors exhibited by the indicator.

A particularly preferred optional component of the present invention is a buffer. As stated earlier, the initially wet indicating composition is adjusted to a pH at least one pH unit below the $pK_a$ of the indicator used. Thus, preferably, the pH of the present composition is from about 5.0 to about 6.5, more preferably from about 5.0 to about 6.0. This pH of the final composition is preferably effected by the addition of a suitable buffer. Such buffers are well known in the chemical art, including the use of such weak acid salts as a sodium bisulfate, sodium acetate and sodium phosphate.

The total amount of buffer incorporated in the indicating composition will depend upon the total amount of urea incorporated in the composition, such that the buffer does not prevent sufficient change in the composition pH (resulting from hydrolysis of the urea present) so as to cause a change in the color of the indicators used. However, the buffer is preferably present in a concentration sufficient to prevent substantial changes in composition pH, and (hereby) spurious indicator color changes, due to chemicals other than urease enzyme in the gastric material sample to be analysed. Typically, then, the buffer is incorporated in the present composition of concentrations of from about 50 to about 2000 milligrams per liter. As used herein, the buffer concentration includes the concentration of the buffer salt and of the acid used to effect pH adjustment of the composition.

Bactericide may also be optionally incorporated in the indicating composition. The bactericide may be one or more materials which substantially inhibit the growth of urease-producing organisms in the indicating composition. Suitable bactericides include sodium azide and methylhydroxybenzoate. Methylhydroxybenzoate is a particularly preferred bactericide. The specific amount of bactericide to be used depends upon factors well known in the microbiological arts, such as the particular bactericide used, and the bactericidal properties (if any) of the other components in the present compositions.

A gelling agent may also be optionally incorporated in the initially wet indicating composition, preferably in the concentration of between about 5 to 50 grams per liter.

As used herein, "gastric material" refers to any moist material obtained directly or indirectly from the upper gastrointestinal tract of a human or other mammal. Such materials include, for example, gastic epithelium, gastic mucosa, and digestive fluids. Samples of such materials, for the use in the method of this invention, may be obtained by a variety of well known methods, according to sound medical practice. Such methods include, for example, obtaining the sample by biopsy of the subject, obtaining the sample from vomitus of the subject, and obtaining the sample from nasal gastric aspirate.

As used herein, "contacting" the sample with the composition of the present invention, as in step (b) of the method set forth above, refers to any method which effects substantial interface between a dry indicating composition (of the type described earlier to detect urease), and the sample gastric material, for a time sufficiently long so as to allow the hydrolysis of urea by any urease present in the sample. Such time is typically longer than about five minutes. Also, preferably, care is taken so as to avoid contamination of the gastric material sample with organisms from a source other than the stomach of the subject to be diagnosed.

In the event that the gastric material used constitutes digestive fluids, then a preferred optional step in the present method is testing the pH of said gastric material. Preferably, then, the sample is contacted with a pH-test composition which is an aqueous solution of the particular indicator used in said composition of this invention (without urea), adjusted to the same pH as said urea-containing dry indicating composition. If the gastric material effects no change in the indicator color of the pH-test composition, then the material is of an acid pH, and may be used directly in the contacting step of the process of this invention described above. If, however, the color of the pH-test composition changes, then the pH of the gastric material must be acidified, as by addition of an acid.

The observing step of this method entails detection of any color change in the composition color, to the color exhibited by the indicator in its dissociation state. Failure of the composition to change color after about twenty-four hours reflects a negative test result.

The following non-limiting examples illustrate the compositions, methods and apparatus of the present invention.

EXAMPLE 1

A composition, according to this invention, was made comprising the following components:

| Component | Quantity (grams) | Final Concentration |
| --- | --- | --- |
| urea | 3.000 | 30 g/l |
| phenol red | 0.008 | 80 mg/l |
| methyl hydroxy benzoate | 0.200 | 2 g/l |
| citric acid | 0.040 | 400 mg/l |
| sodium phosphate | 0.080 | 800 mg/l |

The components, except urea, were dissolved in 100 milliliters of water, heated to approximately 65° C., and stirred until the solution was clear. The solution was then cooled to below approximately 45° C., the urea added and stirred, and the solution pH was measured to be 6.0. The composition was then poured onto paper, a device of this invention, and the paper placed in an incubator set at 40° C. The composition on the paper was allowed to dry, forming a dry indicating composition on the paper having a deep yellow color. The paper was then cut into circles of 10 millimeter diameter.

A dry indicating composition made as above is used in a method of this invention, by obtaining a sample of gastric mucosa from the stomach of a human subject presenting symptoms of gastritis. The mucosa sample is then placed on the dry indicating composition and the color of the test paper observed. After approximately 15 minute, a red color is observed to completely cover the 10 millimeter diameter circle, indicating the presence of Helicobacter-mediated gastrointestinal disorder.

EXAMPLE 2

A composition is made, according to the present invention, comprising the following components:

| Component | Quantity (grams) | Final Concentration |
| --- | --- | --- |
| urea | 2.000 | 20 g/l |
| phenol red | 0.006 | 60 mg/l |

The components were dissolved in 100 ml water, and the pH adjusted to pH 6.2

Approximately 0.5 milliliters of the composition is poured onto paper and is dried in an incubator thus forming a dry indicating composition absorbed into the paper. The dried treated paper was then cut into circles of 15 millimeters diameter as indicated in the preferred embodiments the test apparatus earlier described.

A sample of vomitus from a human infant subject suspected of having gastritis, is drawn into a syringe, and a portion injected into a pH-test composition containing 0.6 milligrams of phenol red in 10 ml of water, adjusted to pH 6.2 the color of the pH-test composition does not change. Thereafter, the remainder of the vomitus sample is injected onto the paper containing the dry indicating composition. The color is observed for approximately 20 minutes, noting a change in color from deep yellow to red, and indicating the presence of gastrointestinal disorder.

What is claimed is:

1. A testing apparatus for detecting urease in a gastric material taken from a mammal, said apparatus comprising a dry indicating composition responsive to said urease, said dry indicating composition being absorbed or impregnated into or applied to a backing sheet or absorbed or impregnated into or applied to a wafer carried by a backing sheet, a cover sheet sealingly adhered about its periphery to said backing sheet to enclose said dry indicating composition, at least one of said backing sheet or said cover sheet has a transparent portion in alignment with said dry indicating composition, said apparatus being arranged such that a sample of said gastric material is applied to one side of the indicating composition and an opposite side of said indicating composition is viewed through said transparent region to determine if a color change has occurred, said backing sheet or wafer having a thickness to provide sufficient buffering capacity to neutralize acid present in said gastric material, and wherein said apparatus can be stored at room temperature.

2. A testing apparatus as claimed in claim 1, wherein said dry indicating composition is absorbed or impregnated into or applied to said backing sheet.

3. A testing apparatus as claimed in claim 1 wherein said dry indicating composition is absorbed or impregnated into or applied to a wafer adhered to said backing sheet.

4. A testing apparatus as claimed in claim 1, wherein said wafer of backing sheet to which said dry indicating composition is absorbed or impregnated comprises a paper have a weight of approximately 90 gsm.

5. A testing apparatus as claimed in claim 1, wherein said dry indicating composition, prior to drying comprises a liquid composition of:
   (a) urea;
   (b) an indicator having a $pK_a$ of from about 6.5 to about 8.5 at an effective concentration; and
   said liquid composition has a pH from about 5.0 to about 6.5, being at least about one pH unit lower than the $pK_a$ of said indicator.

6. A testing apparatus as claimed in claim 5, wherein said indicator is present at a concentration of 2 to about 100 milligrams per liter.

7. A testing apparatus as claimed in claim 5, wherein said indicator is one of p-nitrophenol, bromothymol blue, phenol-red, neutral red, quinoline blue, cresol purple and thymol blue.

8. A testing apparatus as claimed in claim 5, wherein said urea is present at a concentration of about 10 to about 40 grams per liter.

9. A testing apparatus as claimed in claim 5, wherein said composition comprises a buffer.

10. The testing apparatus of claim 5, wherein said indicator has a $pK_a$ from about 7 to about 8.

11. The testing apparatus of claim 5, wherein said liquid composition has a pH from about 5 to about 6.

12. The testing apparatus of claim 8, wherein said urea is present at a concentration of from about 20 to about 40 grams per liter.

13. A method for detection of a gastrointestinal disorder in a mammal by detection of urease in gastric material of the mammal, comprising the steps of:
   (a) providing a testing apparatus as claimed in claim 1;
   (b) obtaining a sample of gastric material from said mammal;
   (c) contacting said dry indicating composition with said gastric sample; and
   (d) observing the color change of said dry indicating composition sample; wherein a change of color of said composition indicates the presence of urease and the existence of a gastrointestinal disorder in a mammal.

14. A method as claimed in claim 13, further comprising the steps of unsealing the transparent cover, contacting said sample with said dry indicating composition, resealing the transparent cover, observing the color of said composition, wherein a change of color of said composition indicates the presence of urease and the existence of a gastrointestinal disorder in the mammal.

15. The method of claim 14, wherein in step (c) said sample of gastric material is applied to one side of a wafer or backing sheet to which said dry indicating composition is absorbed or impregnated, following which said sample permeates said wafer or backing sheet, and in step (g) said color is observed by viewing the opposite side of said wafer or backing sheet to that on which said sample was applied.

16. The method of claim 14, wherein said indicator has a $pK_a$ from about 7 to about 8.

17. The method of claim 14, wherein said liquid composition has a pH from about 5 to about 6.

* * * * *